United States Patent
Wess, Jr.

[11] Patent Number: 6,163,781
[45] Date of Patent: *Dec. 19, 2000

[54] OBJECT-TO-RELATIONAL DATA CONVERTER MAPPING ATTRIBUTES TO OBJECT INSTANCE INTO RELATIONAL TABLES

[75] Inventor: Bernard P. Wess, Jr., Needham Heights, Mass.

[73] Assignee: Physician WebLink Technology Services, Inc., Waltham, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/927,870

[22] Filed: Sep. 11, 1997

[51] Int. Cl.$^7$ .................................................. G06F 17/30
[52] U.S. Cl. .............................. 707/103; 707/2; 707/100; 707/102; 707/509; 705/2
[58] Field of Search ...................... 707/10, 1–5, 100–104, 707/200–204, 509; 395/500, 200.35; 705/2–4, 1–5

[56] References Cited

U.S. PATENT DOCUMENTS

| | | | |
|---|---|---|---|
| 5,295,256 | 3/1994 | Bapat ........................................... | 707/3 |
| 5,426,780 | 6/1995 | Gerull et al. ................................. | 707/3 |
| 5,513,348 | 4/1996 | Ryu et al. .................................... | 707/1 |
| 5,542,078 | 7/1996 | Martel et al. ............................. | 707/101 |
| 5,561,793 | 10/1996 | Bennett et al. .......................... | 707/201 |
| 5,566,333 | 10/1996 | Olson et al. .............................. | 707/102 |

(List continued on next page.)

FOREIGN PATENT DOCUMENTS

0531889A2  3/1993  European Pat. Off. .................... 15/42

OTHER PUBLICATIONS

Steenhagen et al,"Implementation of the object–oriented data model" Technical Report ISSN–0924–3755; Report No. Memo–Inf–91–94; ETN–92–91585. Date unknown. Abstract.

(List continued on next page.)

*Primary Examiner*—John Breene
*Assistant Examiner*—Srirama Channavajjala
*Attorney, Agent, or Firm*—Hayes, Soloway, Hennessey, Grossman & Hage, PC

[57] ABSTRACT

A computerized data processing system and method are provided. One embodiment of the system of the present invention includes a computer-readable memory for storing a definitional data table for defining variable symbols representing respective measurable physical phenomena. The definitional data table uniquely defines the variable symbols by relating them to respective data domains for the respective phenomena represented by the symbols. The system also includes a comparator for signaling existence of a match condition if both a symbolic description in an object instance describing at least one measured phenomenon matches one of the variable symbols in the table and an actual value, also in the object instance, of the at least one measured phenomenon conforms to a respective data domain defining the one variable symbol in the table. A object-to-relational data converter is provided for mapping the attributes of the object instance into two relational tables stored in the memory, an observation table and a measured value table, if the match condition is signaled by the comparator. The converter maps the symbolic description from the object instance into the observation table in association with a unique identification number for the object instance, and also maps the respective data domain and the actual value into the measured value table in association with the unique identification number. Particular utility for the present invention is found in processing, storing, and retrieving of heath-care related in and from, respectively, very large database systems, although other utilities are also contemplated for the present invention.

23 Claims, 7 Drawing Sheets

U.S. PATENT DOCUMENTS

| | | | |
|---|---|---|---|
| 5,604,898 | 2/1997 | Saijyo et al. | 707/4 |
| 5,604,899 | 2/1997 | Doktor | 707/3 |
| 5,615,362 | 3/1997 | Jensen et al. | 707/103 |
| 5,615,367 | 3/1997 | Bennett et al. | 707/102 |
| 5,617,567 | 4/1997 | Doktor | 707/2 |
| 5,627,979 | 5/1997 | Chang et al. | 345/335 |
| 5,630,121 | 5/1997 | Braden-Harder et al. | 707/102 |
| 5,694,598 | 12/1997 | Durand et al. | 707/103 |
| 5,724,575 | 3/1998 | Hoover et al. | 707/10 |
| 5,845,276 | 12/1998 | Emerson et al. | 707/2 |

OTHER PUBLICATIONS

Derringer, "50 Million Parts no Object for Adra's Matrix"; Mass High Tech 14; Newspaper article, p. 1. Aug. 26, 1996 Issue No. 28. Abstract.

Derringer, "Ontos makes price cuts an object for its software" Mass High Tech 14, p. 3. May 13, 1996. Newspaper article. Issue No. 13. Abstract.

Navarra, "Sterling Software Ships". Business Wire, report, p. 1. Mar. 25, 1996. Abstract.

Linthicum, "Objects Meet Data". DBMS, vol. 9, No. 11, p. 72–75. Sep. 9, 1996. Abstract.

Cox, "Software Gives Object Apps Access to DMBs". Communication Week, vol. 531. Nov. 14, 1994. Abstract.

Stodder. "Slouching Toward Middleware". Database Programming & Design, vol. 7, No. 9. pp. 7–8. Sep. 1, 1994. Abstract.

Hayes, et al. "Integrating objects with relational databases". Enterprise Systems Journal, vol. 12, No. 2, pp. 24–29. Feb., 1997. Abstract.

Linthicum. "Object meets data". DBMS vol. 9, No. 10, pp. 72–75. Sep., 1996. Abstract.

Ricciuti. "Object databases find nich as middleware". Info World, vol. 17, No. 46, p. 58. Nov. 13, 1995. Abstract.

Tennant. "Oracle8 Update". Info World, vol. 17, No. 16, p. 25. Apr. 17, 1995. Abstract.

Urban et al. "The design and translation of ORL: an object retrieval language". Journal of Systems and Software, vol. 24, No. 2, pp. 187–207. Feb., 1994. Abstract.

Ricciuti. "RDBMS vendors face an object future". Datamation, vol. 38, No. 22, pp. 40–45. Nov. 1, 1992. Abstract.

Kamada et al. "A general framework for visualizing abstract objects and relations". ACM Transactions on Graphics, vol. 10, No. 1, pp. 1–38. Jan., 1991. Abstract.

Kung. "Object subclass hierarchy in SQL: a simple approach". Communications of the ACM, vol. 33, No. 7, pp. 117–125. Jul., 1990. Abstract.

Monk et al. "Migration from relational to object–orientated databases". Information and Software Technology, vol. 38, No. 7, pp. 467–475. 1996. Abstract.

Yu et al. "Translation of object–oriented queries to relational queries" Proceedings—IEEE Int. Conference on Data Engineering 1995, pp. 29–97. 1995. Abstract.

Getta. "Translation of Extended Entity–Relationship database model into object–oriented database model". IFIP Transations A: Computer Science and Technology n A–25 1993, pp. 87–100. 1993. Abstract.

Yan et al. "Translating relational schema with constraints into OODB schema". IFIP Transactions A: Computer Science and Technology n A–25 1993. pp. 69–85. 1993. Abstract.

Hsieh. "Capturing the object–oriented databases model in relational form". Proceedings—IEEE Computer Society's International Computer Software & Applications, pp. 202–208, 1993. Abstract.

Product description. "Ontos OIS (Object Integration Server)". Feb. 19, 1996. Abstract.

Markowitz et al. "Object queries over relational databases: Language, Implementation, and applications". 1993 IEEE 9th International Conference on Data Engineering, pp. 71–80. 1993. Abstract.

Czejdo et al. "Integration of object–oriented programming languages and database systems in KOPERNIK". Data Knowl. Eng., vol. 7, No. 4, pp. 271–298. Mar. 4, 1992. Abstract.

LaMonica. "Java–based development tools percolate". InfoWorld, vol. 18, No. 10, p. 14. Mar. 4, 1996. Abstract.

Hayes. "Persistence Software slims object–to–relational translator". Computerworld, vol. 29, No. 47, p. 82. Nov. 20, 1995, Abstract.

Richman. "DBConnect helps with relational data access". Computerworld, vol. 29, No. 47, p. 81. Nov. 20, 1995. Abstract.

Urban et al. "The design and translation of ORL: An object retrieval language". Journal of Systems & Software, vol. 24, No. 2, pp. 187–206. Feb., 1994. Abstract.

No Author. "Object Design Partners with Industry Leaders to Provide Web Developers with Richest Possible Multimedia Data Management Solutions". PR Newswire, Burington, Mass. Dec. 9, 1996.

No Author. "Powersoft Launches Powerbuilder 5.0" PR Newswire, Concord, Mass. May 6, 1996. Abstract.

No author. "Sterling Software Ships Key: Workgroup Version 1.5; New Version Provides Seamless Link . . . " Business Wire, Atlanta. Mar. 25, 1996.

No Author. "Passage Systems Deploys ODBMS for Electrical Library; PassagePRO Provides Corporations with Object–Based Online . . . " Business Wire, Menlo Park, Calif. Feb. 26, 1996.

No Author. "VMARK Software, Inc. Announces Fourth Quarter/Year–end 1995 Results; Board of Directors Authorizes . . . " Business Wire, Westboro, Mass. Jan. 25, 1996.

Stephen TC Wong, et al., A hospital integrated framework for multimodality image base management, IEEE 1996, and 455–469, Jul. 1996.

P.Fitsilis et al., Producing relational database schemata from an object oriented design, IEEE 1994, and 251–257, Sep. 1994.

| Tuple Index | Variable Symbol | Variable Symbol ID Number | Data Type | Definitional Description |
|---|---|---|---|---|
| | | | Data Domain | |
| 1 | bp-systolic | 100 | Integer | Systolic Blood Pressure in mm/Hg |
| 2 | bp-diastolic | 200 | Integer | Diastolic Blood Pressure in mm/Hg |
| 3 | Children | 300 | List Text | List of Children |
| 4 | MRI | 400 | MRI Scan Image | MRI Image in Bit Stream Form |
| 5 | Eye-Color | 500 | String | Eye Color |
| •••• | •••• | •••• | •••• | •••• |

| Tuple Index | Object ID # | Variable Symbol/ Symbolic Desc. ID # | Observation | Provider | Person Name | Visit | Date | Person ID # |
|---|---|---|---|---|---|---|---|---|
| 1 | 1 | 200 | 1 | 123 | Smith | 1 | 1993/10/23 | 520 |
| 2 | 2 | 100 | 1 | 123 | Smith | 1 | 1993/10/23 | 520 |
| 3 | 3 | 300 | 1 | 123 | Smith | 1 | 1993/10/23 | 520 |
| 4 | 4 | 400 | 1 | 123 | Smith | 2 | 1993/10/23 | 520 |
| 5 | 5 | 300 | 1 | 125 | Jones | 1 | 1993/10/23 | 601 |
| 6 | 5 | 500 | 1 | 125 | Jones | 1 | 1993/10/23 | 601 |
| ....... | ....... | ....... | ....... | ....... | ....... | ....... | ....... | ....... |

| Tuple Index | Object ID # | Datatype | Value Text String | Value Numerical | Variable Symbol ID # |
|---|---|---|---|---|---|
| 1 | 1 | Integer | "80" | 80 | 200 |
| 2 | 2 | Integer | "120" | 120 | 100 |
| 3 | 3 | String | "jen" | <Null> | 300 |
| 4 | 3 | String | "phil" | <Null> | 300 |
| 5 | 4 | MRI Scan Image | <Null> | <Image 1-Pointer> | 400 |
| 6 | 4 | MRI Scan Image | <Null> | <Image 2-Pointer> | 400 |
| 7 | 5 | String | "bill" | <Null> | 300 |
| 8 | 5 | String | "bob" | <Null> | 300 |
| 9 | 5 | String | "blue" | <Null> | 500 |
| ...... | ...... | ...... | ...... | ...... | ...... |

$o_1 \Rightarrow \{\{$ ("Smith", 1993/10/23), [ $\{\{$ bp-diastolic = (80) $\}\}$ ] , 123 $\}\}$
         200         202                204                        206  208

$o_2 \Rightarrow \{\{$ ("Smith", 1993/10/23), [ $\{\{$ bp-systolic = (120) $\}\}$ ] , 123 $\}\}$
         200         202                204                        206  208

$o_3 \Rightarrow \{\{$ ("Smith", 1993/10/23), [ $\{\{$ children = ( [ "jen" , "phil" ] ) $\}\}$ ] , 123 $\}\}$
         200         202                204                  206    206         208

$o_4 \Rightarrow \{\{$ ("Smith", 1993/10/23), [ $\{\{$ MRI = ( [ <bit stream image data (1)> ,
         200         202                204              206
<bit stream image data (2)> ] ) $\}\}$ ] , 123 $\}\}$
                                      208

$o_5 \Rightarrow \{\{$ ("Jones", 1993/10/23), [ $\{\{$ children = ( [ "bill" , "bob" ] ) $\}\}$ ] , 125 $\}\}$
         200         202                204                  206     206        208
( [ "blue" ] ) $\}\}$ ] , eye color =
    206                    204

OBJECT-TO-RELATIONAL DATA CONVERTER MAPPING ATTRIBUTES TO OBJECT INSTANCE INTO RELATIONAL TABLES

BACKGROUND OF THE INVENTION

1. Field of the Invention

The present invention relates generally to computerized data processing systems and methods, and more specifically, to computerized database systems and methods wherein data from object-oriented data models are mapped into relational data models optimized for very large and complex databases. The present invention finds general utility in areas of information storage where the data is complex or rapidly changing. The present invention finds particular utility in the field of processing, storing, and retrieving heath-care related data (and will described in connection with such utility) in and from, respectively, very large database systems (e.g., systems having storage on the order of 1000 gigabytes or more), although other utilities are also contemplated for the present invention, including processing, storage and retrieval of other types of data.

2. Brief Description of Related Prior Art

Conventional Relational and Object Oriented Database Methodologies

Various means and methodologies exist presently for persistent storage of data for use in computer system applications. Known computer database systems and methods support, inter alia, "schema management" for describing properties of, and relationships between, data in the database.

With the evolution of database technology, fundamental functionality as described hereinbefore has been maintained and expanded while data complexity and processing performance requirements have increased. A type of data management technology applied in commercial data processing known as "relational" database technology is modeled such that all data is organized as though it is formatted into tables, with the table columns representing the table's fields or domains and the table rows representing the values of the table's fields or domains. Data is logically organized as tables but is not necessarily physically stored as such. The relational database user does not need to know how the database is physically constructed and can access and update data via a language interface or "structured query language" (SQL). The relational model assumes a certain stability in the number of columns of data associated with a table and that usually, data is present in most, if not all, fields within the table.

The increase in relative complexity of data (associated with, e.g. science and engineering problem solving, healthcare, marketing and sales and the evolution of complex data structures and data entities modeled on real-world objects) led to the development of "object oriented" database techniques. Object entities or "objects," are complex data structures which can model real-world entities or relationships among or between entities, and are associated in classes and identified with their informational features (attributes). Objects are effected using object oriented programming languages such as Prolog, C++ and Smalltalk. Objects are more readily classifiable into types, which are easily related to one another in subtype/supertype hierarchies. Object oriented languages and databases permit the programmer and database designer to flexibly define data types as not to be constrained by limited predefined types. Object oriented language types can be associated in classes which can "inherit" attributes and/or behaviors from other classes.

Health Care-Related Data Processing and Storage

Processing and storage of health care-related data has involved a substantial, and ever increasing amount of complexity. For example, given advances in medical science, at present, more than 15,000 measurable, human physical conditions (hereinafter "symptomatic conditions") are known to exist which are symptomatic of heath care-related facts, conditional hypotheses (diagnoses), problems and/or conditions in human beings, and/or from which patient care regimes may be established. The number and complexity of these symptomatic conditions continue to increase at an incredible rate.

Conventional commercial/industrial and health care database management systems typically are based upon the relational database model. Given the number and complexity of symptomatic conditions, this has meant that if a single relational database table of health care-related data is to be constructed, that database table generally must be made to comprise a separate database table column for each of the symptomatic conditions whose measurements may be recorded in the database; typically, this results in creation of a very large relational database table comprising many thousands of columns—or many tables with fewer columns—leading to an overwhelming complexity in terms of both database design and information retrieval. Given that it is highly unlikely that measurements of more than a few of the many thousands of symptom conditions will be relevant to diagnosis or treatment of a given patient's medical condition at any given time, it is also highly unlikely that more than a few of these symptomatic conditions will be measured at any given clinical observation of that patient. This results in the creation of a so-called "sparse matrix" database table wherein many of the row and column entries in the relational table will be empty (i.e., filled only with "null" data values or in the worst case, filled with spaces). Unfortunately, all relational database systems require at least some finite amount of computer memory or mass-storage space (hereinafter "storage space") to store such null values and some cannot store null values at all, thus requiring massive storage of spaces. Disadvantageously, since the total amount of storage space present in a given database system is fixed, storage of the relatively large number of null values typically present in a very large sparse matrix database table undesirably decreases the amount of storage space available in the database system for storage of useful data. Further disadvantageously, such very large sparse matrix database tables typically exhibit relatively poor (e.g., slow and inefficient) data storage and search performance, and in extreme cases, can actually be inoperative.

As an attempt to solve these problems, it has been proposed to implement health care-related relational databases in the form of separate relational database tables, each of which is for storing and retrieving data solely related to a particular class of data, for example, diagnosis or treatment of particular classes of medical conditions (e.g., brain or neurological conditions) and/or to be used by particular classes of medical specialists (e.g., brain surgeons or neurologists). Unfortunately, although this solution is effective, to some degree, in reducing the number of null data values stored in this database system compared to the aforesaid sparse matrix database system, it also results in creation of a large number of separate relational database tables which must be joined together when it is desired to perform certain operations on the database (e.g., global search operations for occurrences of measurements of a given variable across all of the tables comprising the database system). Given the large number of separate relational database tables in the database, this means that such operations will require execution of a large number of table joins. Disadvantageously, this can cause this type of conventional database system to exhibit relatively poor data storage and search performance or, in the extreme, the inability to complete the joins in at all or in a timely manner. Since time of retrieval can be critical in healthcare, this solution may not be practical.

Furthermore, heretofore, adequate means have not been provided for ensuring standardization in the form and content of clinical observation data (e.g., actual clinical measurements of symptomatic conditions) input into the database, or in the definitions of symptomatic conditions whose observation data is stored in the database. Unfortunately, this can result in substantial ambiguity and uncertainty in the meaning of observation data contained in the database, for example, when many symbols are used to define either observational data, e.g., blood pressure, or diagnoses, e.g., high blood pressure. Disadvantageously, this can substantially reduce the usefulness of such observation data contained in the database since users of the data base may need to query many sysmbols instead of one.

Additionally, since present health providers (e.g., physicians, health care organizations, and related support personnel) are almost universally solely acquainted with health care-related database systems predicated upon the relational data model, significant institutional bias exists in the health care industry toward use of relational database methodologies. Thus, any solution to the aforesaid prior art problems that is predicated upon use of object-oriented methodologies must also make use of relational data methodologies at least to the extent necessary to permit same to be accepted and used in the health care industry.

Examples of prior art data processing systems and methods are disclosed in, e.g., Gerull et al., U.S. Pat. No. 5,426,780; Ryu et al., U.S. Pat. No. 5,513,348; Martel et al., U.S. Pat. No. 5,542,078; Olson et al., U.S. Pat. No. 5,556,333; Doktor, U.S. Pat. No. 5,604,899; Jensen et al., U.S. Pat. No. 5,615,362; and, Doktor, U.S. Pat. No. 5,617,567. Unfortunately, all of these prior art systems and methods suffer from the aforesaid and/or other disadvantages and drawbacks.

SUMMARY OF THE INVENTION

Accordingly, the present invention provides a computerized data processing system and method which are capable of overcoming the aforesaid and other disadvantages and drawbacks of the prior art. One embodiment of the system of the present invention includes a computer-readable memory for storing a definitional data table for defining variable symbols representing respective measurable physical phenomena. The definitional data table uniquely defines the variable symbols by relating them to respective data domains for the respective phenomena represented by the symbols. The system also includes a comparator for signaling existence of a match condition if both a symbolic description in an object instance describing at least one measured phenomenon matches one of the variable symbols in the table and an actual value, also in the object instance, of the at least one measured phenomenon conforms to a respective data domain defining the one variable symbol in the table. A object-to-relational data converter is provided for mapping the attributes of the object instance into two relational tables stored in the memory, an observation table and a measured value table, if the match condition is signaled by the comparator. The converter maps the symbolic description from the object instance into the observation table in association with a unique identification number for the object instance, and also maps the respective data domain and the actual value into the measured value table in association with the unique identification number.

One embodiment of the method of the present invention essentially comprises storing in a computer-readable memory a definitional data table for defining variable symbols representing respective measurable physical phenomena. The table uniquely defines the variable symbols by relating the symbols with respective data domains for the respective phenomena represented by the symbols. Respective data objects, each of which contains as respective attributes at least one respective actual data value and symbolic description of the respective actual data value, from a plurality of respective observations are compared with the variable symbols and respective data domains contained in the definitional data table to determine if conformity exists between the respective actual data values and symbolic descriptions in the objects, and the variable symbols and respective data domains contained in the definitional data table, and if such conformity exists, the attributes of each data object are mapped into two relational tables stored in the memory: an observation table and a measured value table. The symbolic descriptions from the matching objects are mapped into respective tuples of the observation table in association with respective, unique identification numbers for the respective matching objects. The respective actual data values and data domains of the symbolic descriptions mapped into the observation table are mapped into measured value table in association with the respective unique identification numbers for the respective matching objects.

In the system and method of the present invention, no null values are stored in the main observation data storage table (thereby substantially decreasing the number of null values that must be stored in accordance with the present invention compared to the prior art), substantially fewer tables need to be joined in order to carry out database storage and search operations, queries may be satisfied with inner joins, and searches for any variable stored from any data object may be conducted within the same table (e.g., the observation table). Additionally, the data storage methodology of the present invention is optimized for data search and retrieval operations by parallel computing systems respectively operating on different tables and/or portions of tables in the system and method of the present invention. Moreover, storage is required in the present invention only for data related to those variables that have been precisely defined in the definitional table. Advantageously, this permits the system and method of the present invention to exhibit substantially improved data storage and search performance and storage efficiency compared to the aforesaid conventional single table sparse matrix and multiple table relational database systems, and also allows the system and method of the present invention not to suffer from the aforesaid type of inoperativeness problems of the aforesaid conventional single table sparse matrix database system or the aforesaid many table join problem. Additionally, since in the present invention the object data is mapped into relational database tables, the present invention makes sufficient use of relational data methodologies to permit the system and method of the present invention to be accepted for use in all industries, and particularly advantageously for the health care industry.

Further advantageously, in the system and method of the present invention, applied to the healthcare industry, as an example, the form and content of stored clinical observation data (e.g., actual clinical measurements of symptomatic conditions), and the definitions of symptomatic conditions whose observation data is stored, may be standardized. This permits the aforesaid problems of ambiguity and uncertainty in the meaning of observation data contained in conventional databases to be substantially eliminated according to the present invention, thereby permitting substantial increase in the usefulness of such observation data stored in accordance with the present invention compared to the aforesaid prior art.

Also advantageously, the present invention is well suited to use with very large databases having extremely large data tables (e.g., in excess of one billion rows), and permits the data tables of the present invention to be substantially more compact (i.e., have substantially fewer columns) than is the case in the aforesaid prior art. This results in the unique ability to actually manage the electronic medical information on actual populations of individuals which, of course, may number in the millions for a healthcare user.

Other features and advantages of the present invention will become apparent as the following Detailed Description proceeds, and upon reference to the Drawings, wherein like numerals depict like parts, and wherein:

It should be appreciated that although the following Detailed Description will proceed with reference being made to preferred embodiments and methods of use, the present invention is not intended to be limited to these preferred embodiments and methods of use. On the contrary, the present invention should be viewed broadly as being limited only as set forth in the accompanying claims.

DETAILED DESCRIPTION OF PREFERRED EMBODIMENTS

With reference now being made to FIGS. 1–7, the structure and operation of one preferred embodiment 100 of the system of the present invention will be described. System 100 comprises a remote computer system or computer network system 116 which is connected via a wide area telecommunications network (e.g., an TCP/IP-based Internet-type of computer network) 114 to wide area network interface 112 of database processing system 115. Remote system 116 preferably is physically located remotely from the processing system 115, at a health care provider location (i.e., a location at which a health care provider provides health care-related services to one or more patients of the provider), and preferably comprises one or more computer systems networked together (e.g., by conventional local or wide area network means, not shown) for permitting human users (not shown) of the system 100 at the health care provider location (not shown) to transmit and receive data to and from, respectively, the processing system 115. More specifically, remote computer system 116 comprises appropriate hardware and software (e.g., personal and/or mainframe computers provisioned with Internet wide area network communications hardware and software (e.g., CQI-based, FTP, Netscape Navigator™ or Microsoft Internet Explorer™ HTML Internet Browser software, and/or direct real-time TCP/IP interfaces accessing real-time TCP/IP sockets) for permitting human users to send and receive data, and to control various operations of the processing system 115, in real-time and/or batch-type transactions, in a manner that will be described more fully below.

Figure 1:
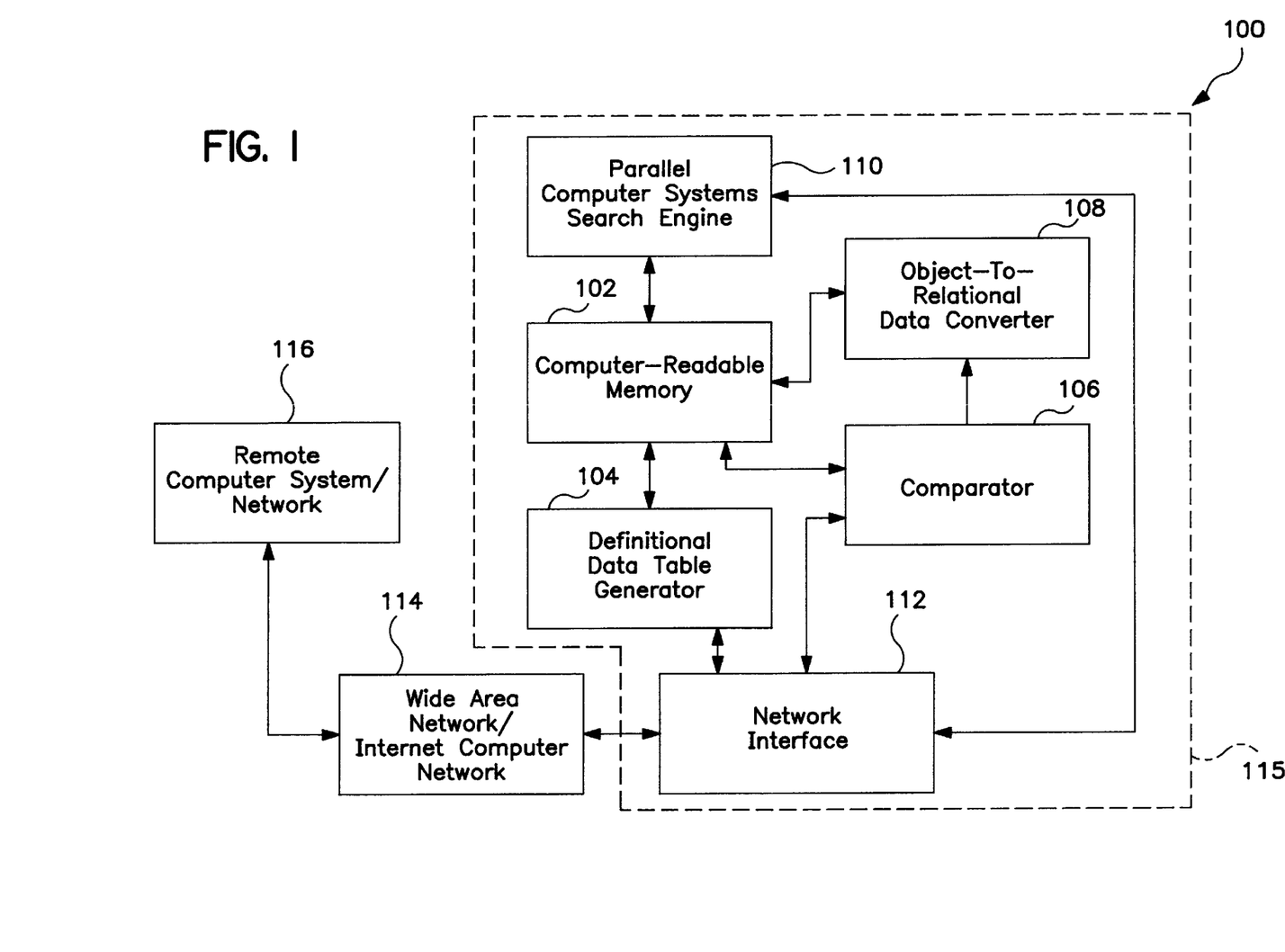
FIG. 1 is an architectural-level, functional block diagram of one preferred embodiment of the system of the present invention.

Network interface 112 converts the format of data and commands received from the remote system 116 via the network 114 into formats suitable for processing by the functional components 104, 106, 108, 110 and/or storage in the computer-readable memory 102 of the processing system 115, and converts the format of data, transmitted from these functional components and memory to the remote system 116 via the network 114, into suitable format for transmission via the network 114 to the remote system 116. Data and/or commands may arrive at the processing system 115 in the following forms: comma delimited data fields within so-called "flat" files, textually-based data objects, ANSI X.12 formatted health care transactions, and/or HL7 health care transactions.

Once data and/or commands are received from the remote system 116 by the interface 112 via the network 114, interface 112 determines which functional component 104, 106, 108, or 110 of the processing system 115 is intended to receive same (i.e., the functional component which is intended to process the data and/or commands) and transmits the data and/or commands to this functional component for processing by said component.

Figure 2:
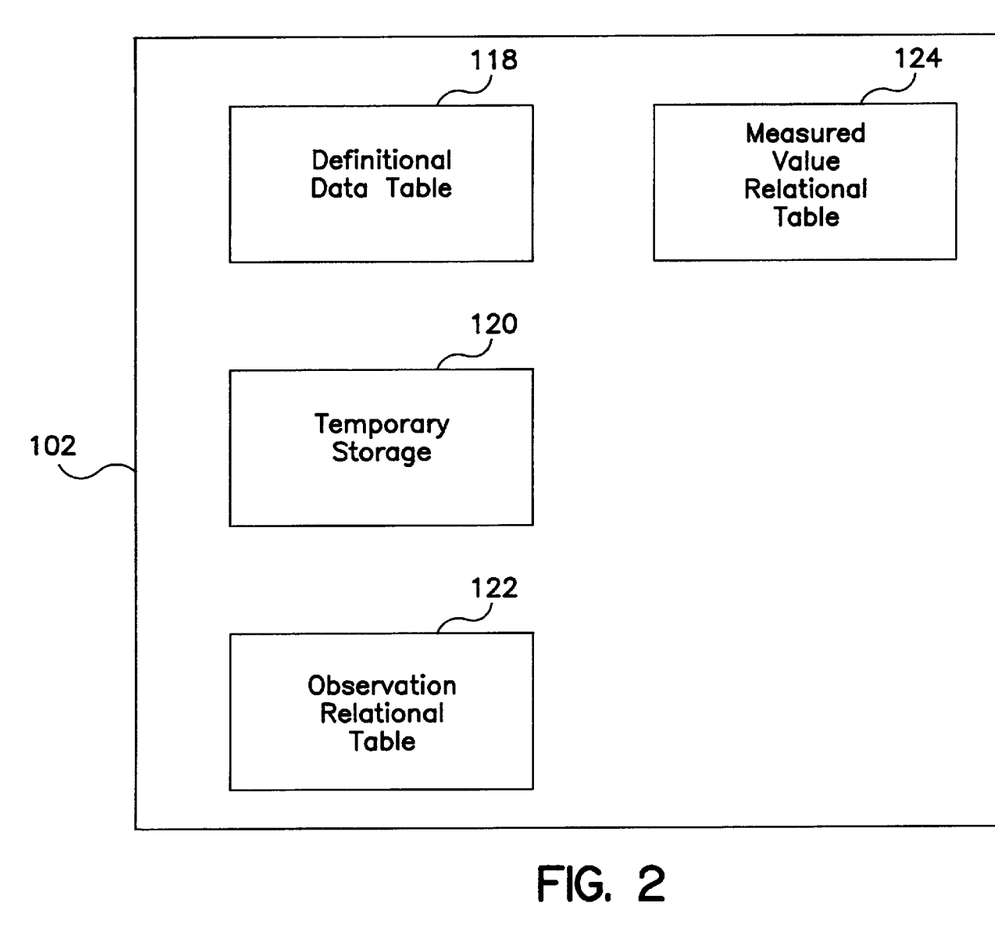
FIG. 2 is an architectural-level block diagram of the computer-readable memory 102 of the system of FIG. 1.
Figure 3:
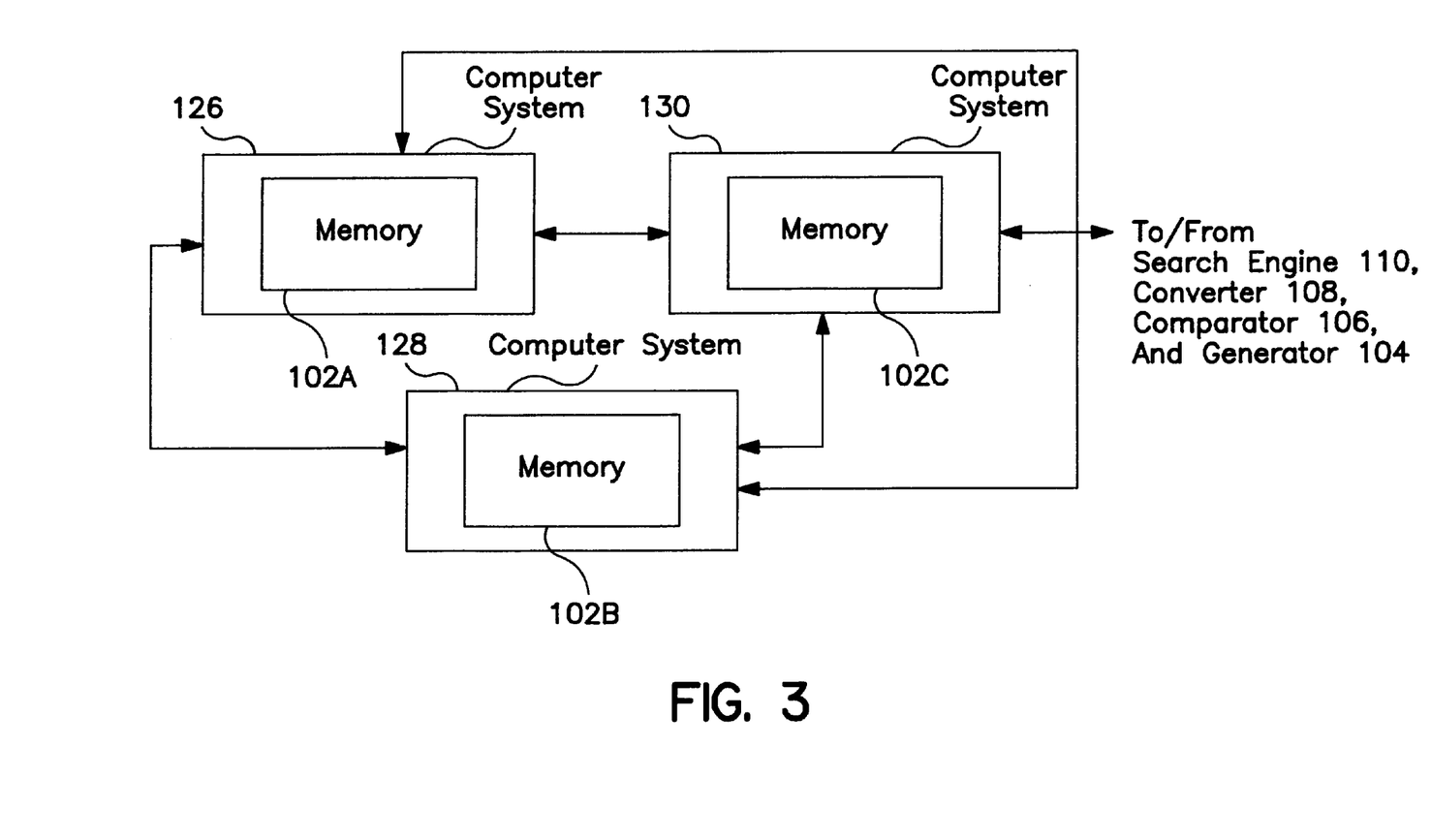
FIG. 3 is a block diagram illustrating in greater detail a preferred configuration of the memory of FIG. 2.

Computer-readable memory 102 is adapted to store and retrieve data to and from definitional data relational table 118, temporary storage memory 120, observation relational table 122, and/or measured value relational table 124 based upon commands received from functional components 104, 106, 108, and/or 110. In this embodiment 100, memory 102 comprises separate computer-readable memories 102A, 102B, 102C comprised in a plurality of separate computer systems 126, 128, 130 networked together via conventional local and/or wide area network means. Each of memories 102A, 102B, 102C comprises conventional volatile and/or non-volatile random access memory and/or mass storage memory devices (e.g., magnetic and/or optical mass storage devices).

Figure 7:
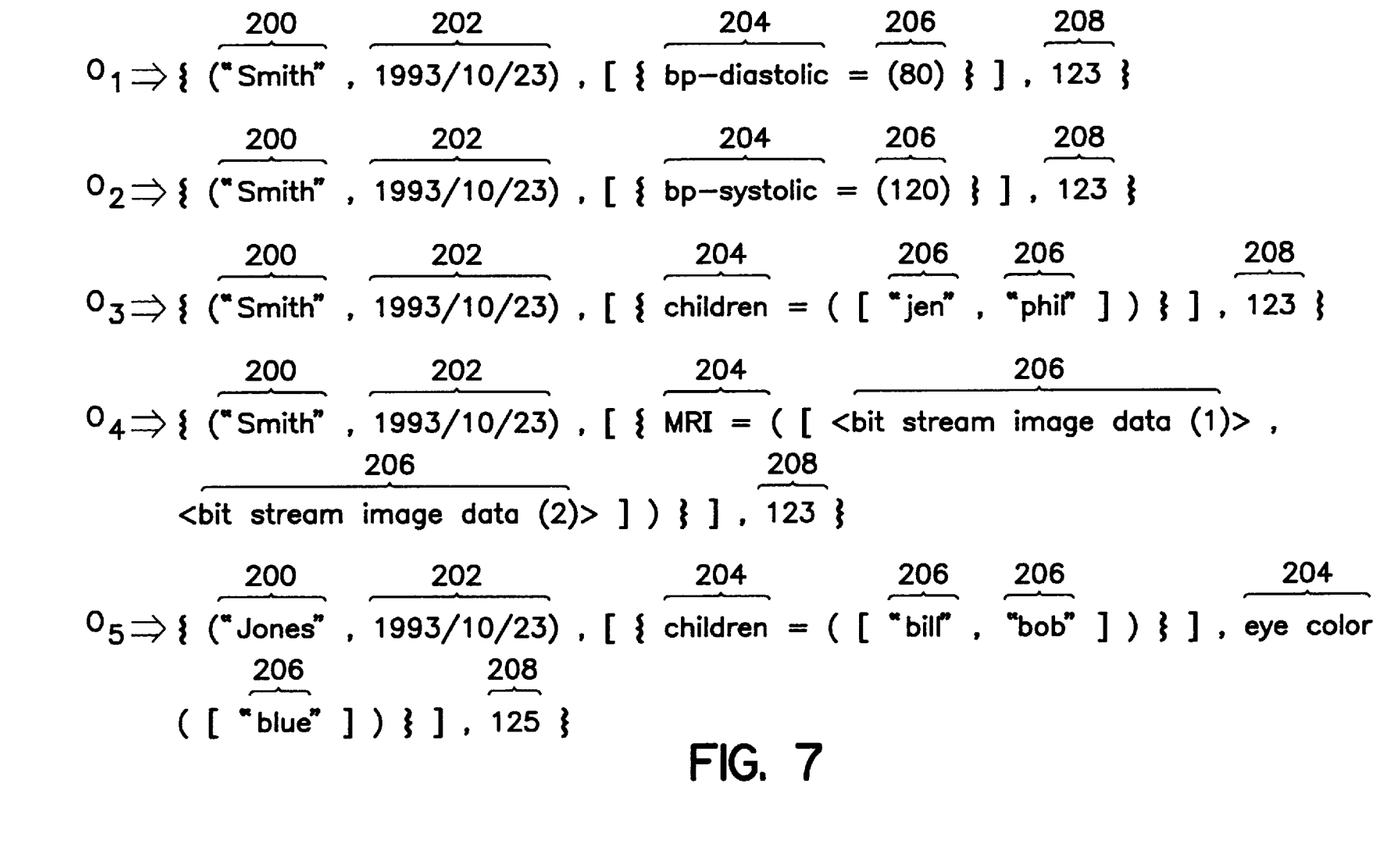
FIG. 7 is a symbolic description of five data object instances processable by the system of FIG. 1.

In accordance with this embodiment of the system of the present invention, data object instances containing data attributes related to measurements of health care-related physical phenomena (e.g., clinical observation data) and ownership relationships of such measurements, and associated processing commands, are transmitted from remote system 116 to interface 112 via network 114 for processing by system 115. Examples of data object instances $O_1$, $O_2$, $O_3$, $O_4$, $O_5$ processable by system 115 are illustrated using symbolic notation in FIG. 7. Of course, the data object examples $O_1$, $O_2$, $O_3$, $O_4$, $O_5$ illustrated in FIG. 7 should not be viewed as being exhaustive, and many different types of object instances (i.e., object instances different from examples $O_1$, $O_2$, $O_3$, $O_4$, $O_5$ illustrated in FIG. 7) may be used in and processed by system 100 without departing from this embodiment of the system of the present invention. As shown in FIG. 7, each object instance $O_1$, $O_2$, $O_3$, $O_4$, $O_5$ generated by and transmitted from the remote system 116 to the processing system 115 includes, as attributes, at least one actual value (e.g., measurement) 206 of at least one respective measured physical phenomenon, a symbolic description 204 of the measured physical phenomenon, and ownership definition 200, 202, 208 data for associating the actual value and symbolic description with the individual (e.g., patient) 200 from which the measurement of the physical phenomenon was derived or to which it pertains, the date 202 of such measurement, and the health care provider 208 who obtained or generated the measurement. In each object instance shown in FIG. 7, the contents of the attributes of the objects are symbolically delimited by position (i.e., order in the object) and by placement of control characters (e.g., braces, parentheses, brackets, and commas). As shown in FIG. 7, for reasons that will become apparent below, in accordance with this embodiment of the system of the present invention, objects processable by the system 100 may include a single actual value 206 associated with a single symbolic description 204 (see object $O_1$ wherein the actual value "80" is associated with the symbolic description "bp-diastolic", and object $O_2$ wherein the actual value "120" is associated with the symbolic description "bp-systolic"), multiple actual values 206 associated with a single symbolic description 204 (see, object $O_3$ wherein the actual values "jen" and "phil" are associated with the symbolic description "children", and object $O_4$ wherein the actual values "bit stream image data (1)" and "bit stream image data (2)" are associated with the symbolic description "MRI"), and/or multiple actual values and multiple symbolic descriptions (see, object $O_5$ wherein the actual values "bill" and "bob" are associated with the symbolic description "children", and actual value "blue" is associated with the symbolic description "eye-color"). Of course, as will be discussed in greater detail below, each object instance may also comprise attributes in addition to the above-described attributes.

When a data object instance and appropriate processing commands are received by the interface 112 from the system 116, the object instance is transmitted by the interface 112 to the comparator 106. Comparator 106 then temporarily stores the object instance in the temporary storage portion 120 of the memory 102 for processing by the functional components 106 and 108.

Figure 4:
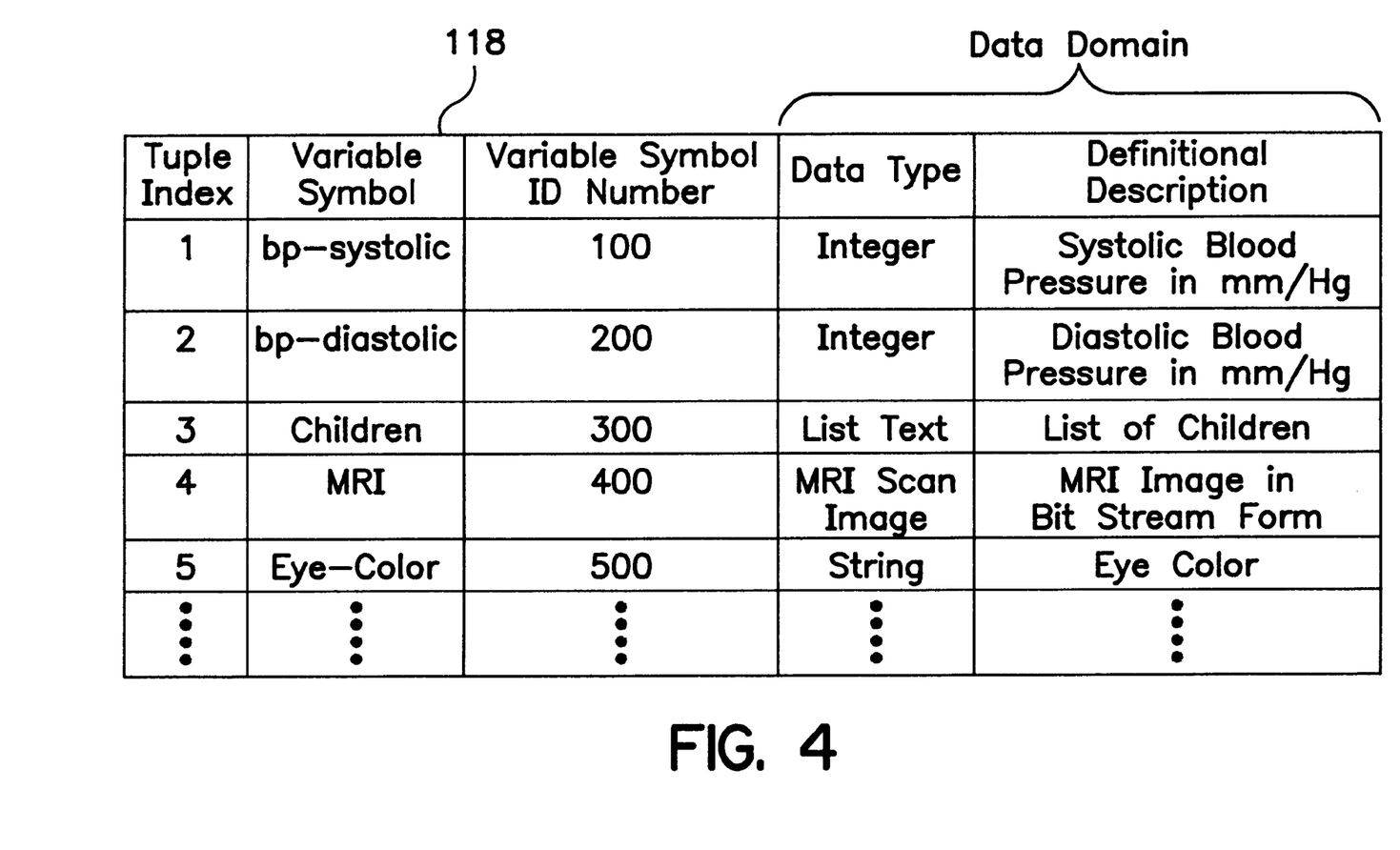
FIG. 4 is a diagrammatic representation of a fragment of the definitional data relational table of the system of FIG. 1.
Figure 5:
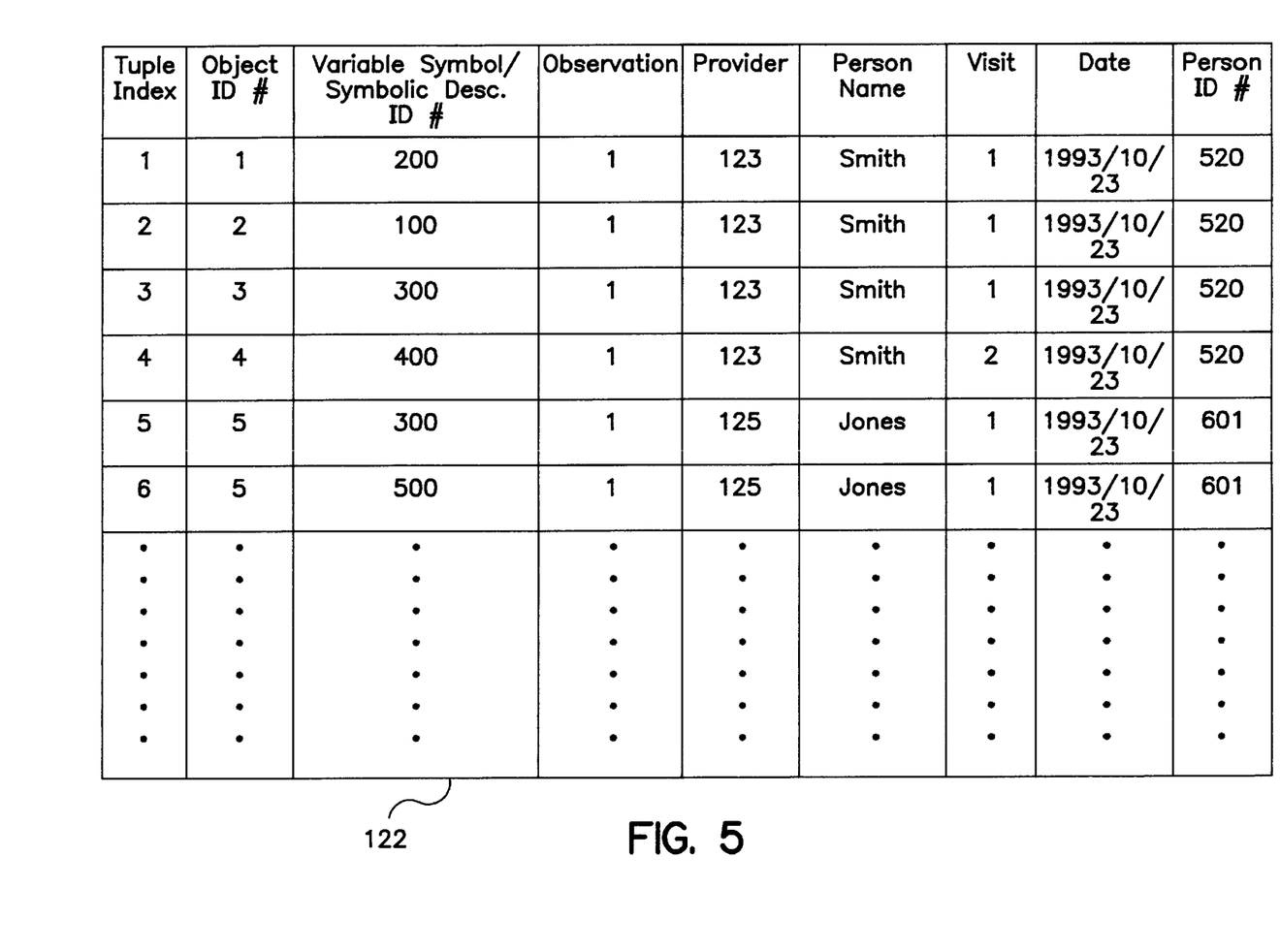
FIG. 5 is a diagrammatic representation of a fragment of the observation data relational table of the system of FIG. 1.
Figure 6:
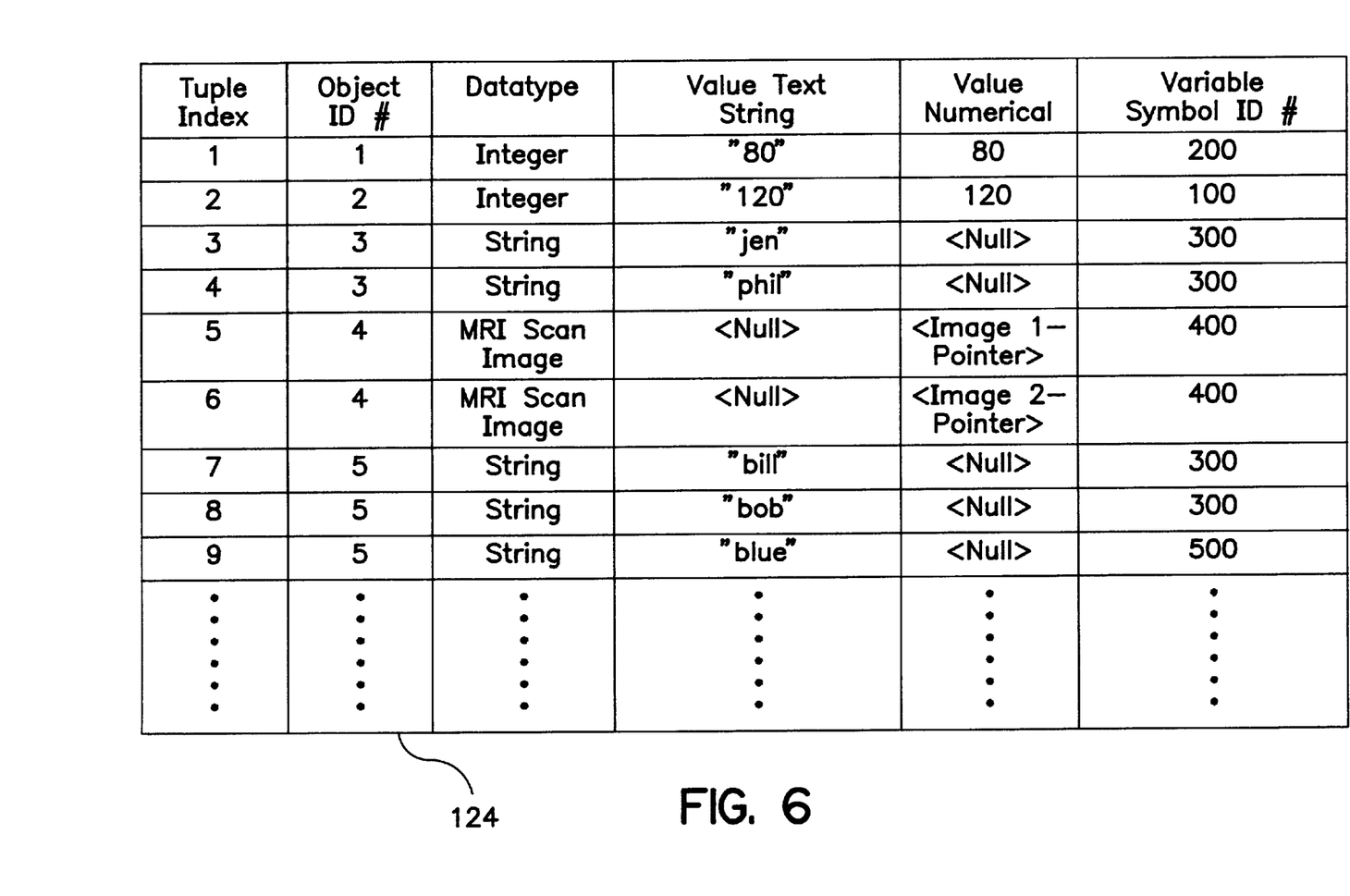
FIG. 6 is a diagrammatic representation of a fragment of the measured value relational table of the system of FIG. 1.

In accordance with this embodiment of the system of the present invention, definitional data table generator 104 generates and stores in memory 102 a definitional data relational table 118 for uniquely defining variable symbols representing respective measurable physical phenomena whose measurements are expected to be supplied to the system 115 in the form of attributes of object instances generated by the system 116. As will be described in greater detail below, table 118 may comprise column entries in addition to those illustrated in FIG. 4. However, as shown in FIG. 4, in this embodiment 100, definitional data table 118 comprises a plurality of tuples (e.g., referenced by tuple index numbers 1–5), each of which defines a respective variable symbol ("bp-systolic", bp-diastolic", "children", "MRI", and "eye-color" in tuples with index numbers 1, 2, 3, 4, and 5, respectively) by associating the respective variable symbol with a respective, unique variable symbol identification number ( "100", "200", "300", "400", and "500" in tuples with index numbers 1, 2, 3, 4, and 5, respectively) and a respective data domain. As shown in FIG. 4, the data domain of each variable symbol comprises two entries: data type and definitional description. The data type entry contains a description of the type of data represented by the variable symbol associated therewith, and in system 100 is selected from the group consisting of: integer (to designate an integer number), real (to designate a real number), text value (to designate the numerical value of a text string), string (to designate a text string), list text (to designate a list of text strings), MRI scan image (to designate a magnetic resonance scan image long binary bit stream), date (to designate a date), voice (to designate an audio voice long binary bit stream), binary (to designate a binary number), float (to designate a floating point number), and video (to designate a video long binary bit stream), x-ray (to designate an x-ray long binary bit stream). Of course, depending upon the type of data represented by the variable symbol being defined in the table 118, other data types may be used in system 100 without departing from the present invention. Also included in the data domain columns of each tuple of the table 118 is a definitional description column for permitting entry of a precise textual definition of each of the variable symbols in the table 118.

Preferably, the data contained in the table 118 is supplied to the network interface 112 from the system 116 via the network 114, together with appropriate commands for causing the interface 112 to forward the data and commands to the generator 104 and to cause the generator 104 to generate and store the table 118 in the memory 102. Alternatively, generator 104 may include a conventional human user interface mechanism (e.g., a direct SQL-type interface, not shown) for permitting a human user to input the data and commands necessary to cause generator 104 to generate and store the table 118 in memory 102.

It is important to note that in generating and storing the table 118 in the memory 102, the generator 104 ensures that each definitional instance of a variable symbol is unique in the table 118 (i.e., generator 104 does not permit more than one definitional tuple entry for any given variable symbol). Likewise, the variable symbol identification number generated by the generator 104 for each of the variable symbols in the table 118 is unique, and is generated by (1) the user by hand, (2) by a software application, (3) by the data base manager embodied within 102 which may, in some cases, automatically generate the tuple index of 118 (ROWID). The primary key for table 118 is the variable symbol.

Returning now to the previous discussion, once a data object instance has been stored in the temporary storage portion 120 of the memory 102, the comparator 106 compares the symbolic description attribute(s) of the object instance with the variable symbols contained in the definitional data table 118 to determine whether a match or matches exist between the attribute(s) and one or more respective symbol(s) in the table 118. For each symbolic description attribute found to match a symbol in the table 118, the comparator 106 compares the actual value attribute (s) associated with the matching symbolic description with the data type entry in the tuple defining the matching variable symbol in the table 118, and signals a match condition for those symbolic description and actual value attributes to the object-to-relational data converter 108 if the actual value attribute(s) conform to the data type specified in the tuple of the table 118 defining the matching variable symbol. If any symbolic description attribute(s) in the object instance does not match one of the variable symbols in the table 118, an "unknown variable condition" is signaled for that attribute and associated actual value(s) by the comparator to the remote system 116 via the interface 112 and network 114. Likewise, if the actual value(s) associated with symbolic description attribute does not conform to the data type specified in the tuple defining a matching variable symbol in the table 118, an "unknown variable data type condition" is also signaled by the comparator 106 to the remote system 116 for those symbolic description and actual data value(s). When an "unknown variable condition" is signaled by the comparator 106 for symbolic description and actual value attributes, remote system 116 may undertake further processing to attempt to rectify the situation (e.g., by indicating occurrence of such condition to human personal (not shown) operating the system) or by returning the actual values in the data object to its source, with error information, through the network interface 112 to the wide-area network/Internet 114 to the original point of transmission in the remote computer system 116.

In order to more fully explain the comparisons made by the comparator 106 to determine whether a match condition should be signaled by the comparator 106 with respect to a specific symbolic description and associated actual value attribute(s), the following discussion is presented with specific reference being made to FIGS. 4 and 7. If comparator 106 were to compare the respective symbolic descriptions and associated actual value attributes of object instances $O_1$, $O_2$, $O_3$, $O_4$, and $O_5$ of FIG. 7 with the variable symbols and data domains contained in FIG. 4, comparator 106 would determine that match conditions exist for all of the respective symbolic descriptions and associated actual value attributes of object instances $O_1$, $O_2$, $O_3$, $O_4$, and $O_5$. More specifically, comparator 106 would determine that the symbolic description and actual value attributes of object instance $O_1$ conform to the variable symbol and associated data domain specified in the tuple having index number 2 in the table 118, the symbolic description and actual value attributes of object instance $O_2$ conform to the variable symbol and associated data domain specified in the tuple having index number 1 in the table 118, the symbolic description and actual value attributes of object instance $O_3$ conform to the variable symbol and associated data domain specified in the tuple having index number 3 in the table 118, the symbolic description and actual value attributes of object instance $O_4$ conform to the variable symbol and associated data domain specified in the tuple having index number 4 in the table 118, and the symbolic descriptions and respective associated actual value attributes of object instance $O_5$ conform to the variable symbols and respective associated data domains specified in the tuples having index numbers 3 and 5, respectively, in the table 118, and in view of this, comparator 106 would signal to the converter 108 respective match conditions for each of the symbolic descriptions and associated actual values in each of the object instances $O_1$, $O_2$, $O_3$, $O_4$, and $O_5$.

If and only if a match condition is signaled to the converter 108 by the comparator 106 for a given symbolic description and actual value(s), converter 108 processes the object instance by mapping the matching symbolic description and actual value(s) attributes of the object instance into two relational tables generated and stored in memory 102 by generator 108: observation relational table 122 and measured value relational table 124. More specifically, the converter 108 generates entries (records) into tables 122 and 124 by sequentially processing (i.e., in the order in which object instances containing matching attributes are signaled by the comparator 106 as containing matching data attributes) the object instances having matching data attributes, and by assigning a unique object identification number to each of the object instances containing the matching attributes; the object identification numbers may be assigned sequentially (i.e., in the same order as processing by the converter 108 of the object instances containing matching attributes) or may be assigned by the converter 108 by (1) assigning a unique number which is the next row identifier available in the data base manager within 102 (ROWID) which can be automatically generated by some data base managers, (2) by incrementing in software by 1 the last row count (N) of the tables in the data base manager 122 and 124 so that the next row object ID is R where R=N+1, or (3) the human user (not shown) or software program (not shown) at remote computer system 116 such that the assigned ID is unique in the universe, in the form of ID=<patient name>+<visit>+<observation>+<julian date>+<time in seconds after midnight>+<random number>. A respective observation number (identifying which sequential observation/measurement of the matching actual value(s) during a given visit by a patient to a health care provider responsible for making the observation/measurement) and a respective visit number (identifying the visit in which the observation/measurement was made) are also assigned by the converter 108 for each matching symbolic description and associated actual value(s) by incrementing by 1 the last observation number for the visit and by incrementing the last visit number by 1 so that the last visit number and last observation number within the visit is always stored within the computer-readable memory 102. A personal identification number identifying the patient from whom the actual value(s) were measured is also assigned by the converter 108 to each matching symbolic description and associated actual value(s) by determining same from a lookup table (not shown) previously stored in memory 102 wherein patient names 200 are associated with respective unique patient identification numbers. Converter 108 also determines from the table 118 the respective variable symbol identification numbers for each of the matching symbolic descriptions, and assigns same to the respective matching symbolic description and associated actual value(s) attributes.

Once the converter 108 has assigned respective object identification, variable symbol identification, observation, visit, and person identification numbers for each matching symbolic description and associated actual value(s) attributes, the converter 108 maps this data, together with various other associated data attributes associated with the matching symbolic description and associated actual value (s) from the object instance containing the matching symbolic description and associated actual value(s), into the tables 122 and 124. More specifically, converter 108 maps the symbolic description from each respective matching symbolic description and associated actual value(s) into an entry in a respective tuple of the table 122 in the sequential order in which the object instance containing said symbolic description was processed; this symbolic description is associated in the respective tuple in table 122 with the respective object identification, observation, health care provider, person identification, and variable symbol identification numbers, and person name associated with that symbolic description. Converter 108 also separately maps each actual value associated with each respective symbolic description stored in table 122 into a respective tuple of the table 124 in the order of processing by the converter 108 of the object instance from which the actual value was taken, and in the sequential order that each said actual value exists in that object instance; each such actual value is stored in its respective tuple of table 124 in association with the respective data type, object identification number, and variable symbol identification number associated with such actual value, and unless the actual of a numerical data type (e.g., integer, real number, etc.), the actual value is stored in one of two columns in the table 124 for storing actual values of string or numerical types, respectively; alternatively, if the actual value is of a numerical data type, the actual value is stored in both of said columns (i.e., is stored in the column for storing numerical data values in its respective numerical data format and in the column for storing string data values cast in the form of a string data value). Actual values for bit stream data types are stored by converter 108 in separate respective tables of contiguous memory locations (not shown) in memory 102, and respective pointers to respective starting memory locations for said tables are stored in the numerical value column of the respective tuples of table 124 associated with such actual values. Each respective tuple of table 124 contain only a single, respective actual value.

Specific examples of the manner in which converter 108 accomplishes the above functions will now be described with reference to FIGS. 2 and 4–7. For purposes of this illustration, it is assumed that the object instances $O_1$, $O_2$, $O_3$, $O_4$, and $O_5$ are processed by converter 108 in the order in which said instances are recited herein (i.e., instance $O_1$ being processed first, followed by processing of instance $O_2$, which in turn is followed by processing of instance $O_3$, and so forth, until instance $O_5$ is processed), and within each object instance, the attributes therein are processed in the order in which they are recited in FIG. 7 (i.e. from left to right in each instance). Converter 108 assigns to each of said instances $O_1$, $O_2$, $O_3$, $O_4$, and $O_5$ a unique respective object identification number equal to the subscript of its object number (i.e., instance $O_1$ is assigned an object identification number of 1, instance $O_2$ is assigned an object identification number of 2, and so forth). The respective health care provider number, date of observation, person identification number, observation number, and visit number for each of the symbolic descriptions and associated value attributes in each of the objects $O_1$, $O_2$, $O_3$, $O_4$, and $O_5$ are determined by the converter 108 in the manner specified above. The respective variable symbol numbers and data types associated with each of the symbolic descriptions in each of the objects $O_1$, $O_2$, $O_3$, $O_4$, and $O_5$ are determined by the converter 108 from the definitional data table 118.

Converter 108 stores the portions of the above data associated with the symbolic description and associated data value from the first-processed object (i.e., object $O_1$) in tables 122 and 124 as follows. In observation table 122, converter 108 generates a first tuple (i.e., having tuple index number 1) wherein are stored in respective columns from left to right, the object identification number (i.e., "1") for object $O_1$, the variable symbol identification number from table 118 for the symbolic description/variable symbol "bp-diastolic" (i.e., 200), the observation number for the actual value associated with this tuple (i.e., "1"), the health care provider specified in the object $O_1$ (i.e., "123"), the patient name specified in the object $O_1$ (i.e., "Smith"), the visit number during which the observation being recorded in this tuple was made (i.e., "1"), the date of said visit or generation of the data being stored in the tuple (i.e., "1993/10/23"), and the person identification number associated with the patient recited in the tuple (i.e., "Smith"). The portions of the above data associated with later-processed objects $O_2$, $O_3$, $O_4$, and $O_5$ are processed, in this order and in the manner specified above, by converter 108 so as to obtain the portion of the relational table 122 shown in FIG. 5.

Converter 108 also generates the first tuple (i.e., having tuple index number 1) of measured value table 124 by placing in respective columns from left to right, the object identification number associated with the first-processed object $O_1$ (i.e., "1"), the data type of the symbolic description/variable symbol of object $O_1$ whose actual value is being stored in the tuple (i.e., "Integer"), the textual value of the numerical actual value being stored in the tuple (i.e., the string "80"), the numerical value of said actual value (i.e., the number 80), and the variable symbol identification number associated with the actual value stored in the tuple (i.e., 200). The actual values contained in each of the objects $O_2$, $O_3$, $O_4$, and $O_5$ are processed by converter 108 in the aforesaid manner specified for generating the table 124, so as to generate the table 124 shown in FIG. 6. It should be noted that in FIG. 6, the term "<NULL>" refers to a null data value, and the terms "<IMAGE 1-Pointer>", <IMAGE 2-Pointer>" refer to memory pointers to the starting locations in memory 102 for tables (not shown) containing bit stream image data (1) and (2), respectively, from object $O_4$.

Processing system 115 also includes search engine 110 for performing queries upon and retrieving matching data from tables 118, 122, and 124 based upon SQL-based queries and search commands provided to engine 110 from system 116 or from a human user computer interface (e.g., a graphical user SQL interface, not shown) comprised within engine 110. Preferably, search engine 110 comprises one or more symmetrically (SMP), massively (MPP) or geographically distributed (through Internet/Intranet) networked parallel computer systems for searching different respective tables or portions of tables 118, 122, 124. Searches of tables 118, 122, 124 maybe made by engine 110 using queries specifying many different search criteria, including patient name or identification number, identification number of the health care provider, variable symbol, date of observation, observation number, etc., and/or based upon combinations of these criteria. Furthermore, nested queries may be executed by engine 110 wherein one or more sub-queries are first executed on one or more of tables 118, 120, 122, 124 to obtain information necessary to execute other or main queries. For example, a nested query may be executed by engine 110 wherein a sub-query is first executed on the definition table 118 to determine the variable symbol identification number of a desired variable symbol for use in a main query to locate entries in the tables 122, 124 associated with a specified search value range for the desired variable symbol. Searches may also be conducted using engine 110 based upon nested queries wherein a sub-query may be executed upon the lookup table (not shown) associating health care providers with respective health care provider identification numbers, so as to locate the identification number of said provider for use in a query of table 122. Similar types of nested queries based upon certain types personal information (i.e., respective social security numbers, residence address, etc.) may also be conducted using a table (not shown) in memory 102 associating such personal information with respective personal names and identification numbers, and order to obtain such names and/or identification numbers for use in other queries upon table 122. It will be appreciated by those skilled in the art that many variations upon the above types of search strategies may be employed using search engine 110 without departing from the present invention.

Thus, as will be appreciated by those skilled in the art, in accordance with the present invention, a logical object-oriented data processing system and method are constructed using the relational data storage model. Thus, it is evident that there have been provided in accordance with the present invention a computerized data processing system and method that fully satisfy both the aims and objectives hereinbefore set forth. It will be appreciated that although the present invention has been described in connection with preferred embodiments and methods of use, many modifications, alternatives, and equivalents will be apparent to those skilled in the art. For example, although the present invention has been described in connection with processing, storage, and retrieval of health care-related data, it will be appreciated by those skilled in the art that other types of data (e.g., other types of complex, sparse matrix data, such as, financial service data, market research data, etc., concerning many different types of variables) may be processed, stored, and retrieved (e.g., in an ad hoc manner) in accordance with the present invention. Furthermore, it should be understood that the variable symbol names and number of said symbols as described above are merely exemplary, and in actual implementation, many thousands or millions of such symbols would be defined and used in system 100. Further, in actual instances each of tables 118, 122, 124 would contain many thousands, if not millions, of tuples.

Other modifications are also possible. For example, preferably, each of the above-presented functional components 104, 106, 108, 110, and 112 is embodied as one or more distributed computer program processes running on one or more conventional general purpose computers networked together by conventional networking hardware and software. Most preferably, each of these functional components 104, 106, 108, 110, and 112 is embodied by running distributed computer program processes (e.g., generated using "full-scale" relational database engines such as IBM DB2™, SQLServer™, Oracle 7.3™ or Oracle 8.0™ database managers) on networked computer systems (e.g., comprising mainframe and/or symmetrically or massively parallel computing systems such as the IBM SB2™ or HP™ 9000 computer systems) including appropriate mass storage, networking, and other hardware and software for permitting these functional components to achieve the stated function. Preferably, these computer systems are geographically distributed and connected together via appropriate wide- and local-area network hardware and software.

Alternatively, the aforesaid functional components may be embodied by a plurality of separate computer processes (e.g., generated via dBase™, Xbase™, MSAccess™ or other "flat file" type database management systems or products) running on IBM-type, Intel Pentium™ or RISC microprocessor-based personal computers networked together via conventional networking hardware and software and including such other additional conventional hardware and software as is necessary to permit these functional components to achieve the stated functionalities. In this alternative configuration, since such personal computers typically are unable to run full-scale relational database engines of the types presented above, a non-relational flat file "table" (not shown) may be included in at least one of the networked personal computers to represent at least portions of the observation table. The flat file "table" may also be used in downloading clinical objects over the Internet computer network to a remote workstation and/or in receiving pre-validated clinical objects over the Internet computer network or other telecommunications media, so as to permit further processing of such objects in accordance with the present invention. Preferably, these personal computers run the Unix, Microsoft Windows NT™ or Windows 95™ operating system. The aforesaid functional components of system 100 may also be comprised by a combination of the above two configurations (e.g., by computer program processes running on a combination of personal computers, RISC systems, mainframes, symmetric or parallel computer systems, and/or other appropriate hardware and software, networked together via appropriate wide and local area network hardware and software).

Other modifications are also possible. For example, the present invention may be part of a larger computerized health care-related information multi-database or multi-computer system or "warehouse" wherein other data types, processing systems (e.g., transaction, financial, administrative, statistical, data extracting and auditing, data transmission/reception, clinical and/or accounting support and service systems), and/or storage methodologies may be used in conjunction with those of the present invention to achieve an overall health care-related information management, processing, storage, search, statistical and retrieval solution for a particular health care provider, health maintenance, or payment system, and/or for a cooperative or network of such systems. Such a health care-related information database warehouse may also include an automated or manual report generator process for periodically generating summary tables and/or reports based upon the data contained in the warehouse, including periodic (e.g., monthly) summary tables and/or reports describing total charges for all medical groups in the provider network for a given reporting period, total membership time for the reporting period for each enrollment group in the network, total Dx and Tx counts for each member or group in the network for the reporting period, and/or total deaths for the period separated according to provider or provider group.

Yet other modifications are also possible. For example, if system 100 is modified in ways apparent to those skilled in the art, remote computer system 116 may instead comprise a local computer system or computer network (i.e., located at the same physical location as the processing system 115), and network 114 may instead comprise a local area network for connecting the local computer system or computer network to the network interface 112.

Still other modifications are possible. For example, although not shown in the Figures, the data objects received by the system 115 may contain data attributes in addition to those described above (e.g detailed information on persons who may become or have been patients (including the not yet born), medical providers of care, their associations, relationships and medical facilities, financial transactions on payments, demographic and market research data, whether related to healthcare or in general, (re)insurance products of providers or management firms, prices and services, each financial transaction, admissions, discharges and transfer of patients, detailed diagnostic and treatment information coded within national and international standards such as the US AMA CPT™ codes, CDC ICD codes, radiology codes, information on medical outcomes (clinical, administrative or financial), morbidity and mortality data, information on medical and insurance normative behavior and comparative data, information to manage disease stages, illness or injury incurred on the job, rehabilitation, worker's compensation and disability information, medical referrals to other providers, expert-systems derived data on demand for upcoming services based on statistically computed values, computed statistical terms of medical and economic risk, measures of risk-sharing among providers and potential or actual professional liability experiences, and definitions of all medically related entities to the healthcare system, including vocabularies, definitions and terms of expression). Similarly, tables 118, 122, and 124 may be modified to incorporate some of all of such additional information and/or memory 102 may contain additional tables relating other types of information for use by system 100. For example, memory 102 may contain additional relational tables relating the aforesaid and other types of additional information, detailed information on persons who may become or have been patients (including the not yet born), medical providers of care, their associations, relationships and medical facilities, financial transactions on payments, demographic and market research data, whether related to healthcare or in general, (re)insurance products of providers or management firms, prices and services, each financial transaction, admissions, discharges and transfer of patients, detailed diagnostic and treatment information coded within national and international standards such as the US AMA CPT™ codes, CDC ICD codes, radiology codes, information on medical outcomes (clinical, administrative or financial), morbidity and mortality data, information on medical and insurance normative behavior and comparative data, information to manage disease stages, illness or injury incurred on the job, rehabilitation, worker'compensation and disability information, medical referrals to other providers, expert-systems derived data on demand for upcoming services based on statistically computed values, computed statistical terms of medical and economic risk, measures of risk-sharing among providers and potential or actual professional liability experiences, and definitions of all medically related entities to the healthcare system, including vocabularies, definitions and terms of expression. Tables 118, 122, and 124 may contain column entries for the aforesaid and other types of additional information.

Accordingly, it is intended that the present invention be viewed quite broadly as encompassing all such modifications, alternatives, and equivalents, and that the present invention be limited only as set forth in the accompanying claims.

What is claimed is:

1. A data processing system, comprising: a computer-readable memory for storing a single definitional data table for defining variable symbols representing respective measurable physical phenomena by relating said symbols with respective data domains for the respective phenomena represented by said symbols, wherein each said variable symbol being defined in a row of said definitional data table; a comparator for signaling existence of a match condition if both a symbolic description in an object instance describing at least one measured phenomenon matches one of said variable symbols in said table and an actual value, also in said object instance, of said at least one measured phenomenon conforms to one respective data domain defining said one variable symbol in said table; and an object-to-relational data converter for mapping attributes of said object instance into two relational tables stored in said memory, if said match condition is signaled by said comparator, one of said relational tables being an observation table and the other of said relational tables being a measured value table, said converter mapping said symbolic description from the object instance into said observation table in association with a unique identification number for the object instance, said converter also mapping said actual value into said measured value table in association with said unique identification number, wherein each instance of said attributes of said object instance being mapped into a row of said observation table or said measured value table.

2. A system according to claim 1, wherein said data domains each include a respective data type and respective definitional description.

3. A system according to claim 1, wherein said definitional data table is a relational data table including a plurality of tuples containing respective numbers uniquely identifying said variable symbols.

4. A system according to claim 3, wherein said observation table is also for associating with said symbolic description one of said respective numbers in said definitional data table identifying said symbolic description.

5. A system according to claim 1, wherein said computer-readable memory is comprised in a plurality of networked computer systems.

6. A system according to claim 1, further comprising at least one remote computer system for being networked to said computerized data processing system via an Internet computer network so as to permit said computerized data processing system to receive said object instance from said remote computer system via said Internet computer network.

7. A system according to claim 1, wherein said measured value table is also for storing in association with said actual value one respective data type of said actual value, said one respective data type being part of said one respective data domain.

8. A system according to claim 1, wherein said data domains each include a respective data type selected from the group consisting of integer, real, string, list, video, audio, and scan image.

9. A system according to claim 8, wherein said one respective data domain includes a scan image data type, said actual value is a bit stream containing data representing a scanned image, and pointers to locations in said memory containing separate portions of said bit stream are stored in a plurality of tuples in said measured value table.

10. A system according to claim 1, wherein said object instance comprises a plurality of symbolic descriptions and a plurality of actual values associated with said plurality of symbolic descriptions for describing a plurality of measured phenomena, and said converter is for mapping said plurality of symbolic descriptions into respective tuples of said observation table such that only a single respective symbolic description is mapped into a single respective tuple of said observation table, each of said respective tuples associating the unique identification number with the plurality of symbolic descriptions mapped into said respective tuples.

11. A system according to claim 10, wherein said measured value table also includes a plurality of tuples, each of said tuples being for storing a respective one of said actual values.

12. A system according to claim 1, wherein no entry of said observation table contains a null data value.

13. A system according to claim 1, further comprising, parallel computing systems for searching respective different portions of at least one of said tables.

14. A computerized data processing system according to claim 13, wherein said at least one of said tables comprises said observation table.

15. A system according to claim 1, wherein said actual data comprises health care patient observation data, said object instance also includes observation identification data, and said converter maps said observation identification data into said observation table in association with said symbolic description and said unique identification number.

16. A system according to claim 15, wherein said observation identification data includes respective visit number and in-visit observation data.

17. A system according to claim 15, wherein said object instance also contains health care provider identification information for identifying a health care provider supplying said object instance, and said converter is also for mapping said health care provider identification information into said observation table in association with said symbolic description, said unique identification number, and said observation identification data.

18. A system according to claim 1, wherein said measured value table includes at least two fields for storing said actual data value, one of said at least two fields being for permitting said actual data value to be stored in numerical data form, the other of said at least two fields being for permitting said actual data value in string data form.

19. A system according to claim 18, wherein, if said actual data value comprises a data string, then said one field contains a null data value and said other field contains said data string.

20. A system according to claim 18, wherein, if said actual data value comprises a data bit stream, then said one field contains a pointer to a location in said memory wherein at least a portion of said stream is located, and said other field contains a null data value.

21. A computerized data processing method, comprising: storing in a computer-readable memory a single definitional data table for defining variable symbols representing respective measurable physical phenomena, said table uniquely defining said variable symbols by relating said symbols with respective data domains for the respective phenomena represented by said symbols, wherein each said variable symbol being defined in a row of said definitional data table; comparing respective sets of actual data values and associated symbolic descriptions, from a plurality of respective data object instances for describing a respective plurality of observations, with the variable symbols and respective data domains in said definitional data table for conformity therewith; and if said conformity exists, mapping attributes of each data object into rows of observation and measured value relational tables stored in said memory such that symbolic descriptions from respective conforming objects are mapped into respective tuples representing rows of the observation table in association with respective, unique identification numbers for the respective conforming tuples, and also such that respective actual data values and data domains of the respective symbolic descriptions are mapped into rows of the measured value table in association with the respective unique identification numbers for the respective conforming objects.

22. A computerized data processing method according to claim 21, wherein each said respective tuple also includes respective observation identification data.

23. A computerized data processing method according to claim 22, wherein said actual data comprises health care patient observation data, and said respective observation identification data includes respective patient visit number and in-visit observation data.

* * * * *